(12) United States Patent
Mayer et al.

(10) Patent No.: US 6,351,390 B1
(45) Date of Patent: Feb. 26, 2002

(54) METHOD FOR APPLYING A MICROSYSTEM OR A CONVERTER ON A SUBSTRATE, AND DEVICE MANUFACTURED ACCORDINGLY

(75) Inventors: Felix Mayer, Zurich (CH); Oliver Paul, Au (DE)

(73) Assignee: Laboratorium fur Physikalische Elektronik Institut fur Quantenelektronik, Zurich (CH)

(*) Notice: Subject to any disclaimer, the term of this patent is extended or adjusted under 35 U.S.C. 154(b) by 0 days.

(21) Appl. No.: 09/331,135

(22) PCT Filed: Dec. 12, 1997

(86) PCT No.: PCT/CH97/00465

§ 371 Date: Jul. 22, 1999

§ 102(e) Date: Jul. 22, 1999

(87) PCT Pub. No.: WO98/27411

PCT Pub. Date: Jun. 25, 1998

(30) Foreign Application Priority Data

Dec. 17, 1996 (CH) .............................................. 3091/96

(51) Int. Cl.⁷ ................................................. H05K 1/18
(52) U.S. Cl. ...................... 361/760; 361/748; 361/764; 361/765; 361/767; 361/772; 174/250; 174/255; 174/259; 174/260; 257/737; 257/778
(58) Field of Search ................................. 361/760, 748, 361/764, 765, 767, 772; 174/250, 255, 259, 260; 257/723, 777, 778, 737, 736, 788, 789

(56) References Cited

U.S. PATENT DOCUMENTS

| 4,763,098 A | 8/1988 | Glenn |
| 4,814,943 A | * 3/1989 | Okuaki ........................ 361/783 |
| 5,258,576 A | * 11/1993 | Neumann et al. ........... 174/52.4 |

(List continued on next page.)

FOREIGN PATENT DOCUMENTS

| EP | 0 543 430 A2 | 5/1993 | |
| EP | 0 654 826 A1 | 5/1995 | |
| EP | 0 709 659 A2 | 5/1996 | |
| JP | 404028260 A | * 4/1998 | ......... H01L/25/065 |
| JP | 410092876 A | * 4/1998 | ........... H01L/21/60 |
| WO | WO93/07457 | 4/1993 | |
| WO | WO98/05935 | 2/1998 | |

OTHER PUBLICATIONS

IBM Technical Bulletin vol. 30 No. 9, Feb. 1998.*

*Primary Examiner*—Leo P. Picard
*Assistant Examiner*—David Foster
(74) *Attorney, Agent, or Firm*—Oppedahl & Larson LLP

(57) ABSTRACT

A process is given for permitting the application to a substrate (2) of a microsystem or transducer (1) having a first partial surface (13), whose interaction with the environment is to be possible, and a second partial surface (14), which is to be protected against external influences. The substrate (2) is prepared, a passage point (20) being produced in said substrate (2). The microsystem (1) and substrate (2) are so mutually positioned that the first partial surface (13) faces the substrate (2) and that the passage point (20) in the substrate (2) and the first partial surface (13) come to rest opposite one another. Contacts (50, 51.1, 51.2) are produced by flip-chip technology. A sealing contact (51.1, 51.2) seals the second partial surface (14) against external influences. A gap (3) between the microsystem (1) and substrate (2) is filled with a filling material (30). A selective cover (24) over the passage point (20) keeps undesired external influences away from the first partial surface (13). The microsystem (1) can e.g. contain a sensor, the first partial surface (13) containing the sensitive surface and the second partial surface (14) electronic functional units.

21 Claims, 4 Drawing Sheets

U.S. PATENT DOCUMENTS

Figure 1:
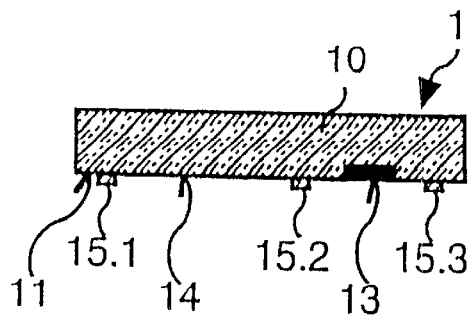

| | | | |
|---|---|---|---|
| 5,385,869 A | * | 1/1995 | Liu et al. ................... 29/841 |
| 5,492,586 A | * | 2/1996 | Gorczyca ................. 156/245 |
| 5,646,828 A | * | 7/1997 | Degani et al. ............ 361/715 |
| 5,766,982 A | * | 6/1998 | Akram et al. ............... 438/51 |
| 5,959,363 A | * | 9/1999 | Yamada et al. ........... 257/787 |
| 6,093,972 A | * | 7/2000 | Carney et al. ............ 257/790 |

* cited by examiner

METHOD FOR APPLYING A MICROSYSTEM OR A CONVERTER ON A SUBSTRATE, AND DEVICE MANUFACTURED ACCORDINGLY

The invention relates to a process for applying a microsystem or transducer to a substrate and to a device which can be produced according to this process in accordance with the preambles of the independent claims.

In the present specification the terms "sensor", "actuator", "transducer" and "microsystem" are, for reasons of simplicity, grouped under the term "system". In the case of many such systems, e.g. in many sensors and actuators, apart from the electrical contacting or bonding, there must be further connections to the environment. Part of the system, e.g. a sensitive surface of a humidity sensor, must consequently be open for external influences, e.g. for the external air to be measured. In other words, there must be a connection between a specific part of the system and the environment, so that said part of the system can interact with the environment. However, at the same time other parts of the system must have a good protection against external influences, e.g. moisture, contaminants, corrosive vapours, etc. Such parts requiring protection are e.g. electrical contacts, electronic functional units, circuits or other sensors, which require no opening, e.g. temperature sensors. Therefore the system must be locally selectively packed.

The following are examples of known production processes for locally selectively packed systems:

Dosing method: With a robot-controlled dispenser a wrapping or enveloping material having the correct viscosity is applied to the system in such a way that the desired surface remains free.

Air flow method: Once again a viscous wrapping or enveloping material is applied to the system. In order to obtain a partial surface free from wrapping material, inert gas is blown through a nozzle onto the sensitive surface in such a way that the flow movement of the wrapping material is stopped over said partial surface.

Capillary method: The system to be packed is covered by a cover sheet, which is kept at a small distance from the surface. The viscous wrapping material is drawn between the cover sheet and the system by capillary forces. An opening is made in the cover sheet above the partial surface to be kept open, so that there the wrapping material flow is stopped due to the lack of capillary force and an opening is obtained in the wrapping material.

UV light method: Use is made of a UV-curing sealing compound. In order to keep open a specific partial surface of the system, said partial surface is intensely irradiated with UV light. On application the sealing compound flows over the unilluminated partial surface of the system, solidifying on the edge of the illuminated partial surface, which consequently remains free.

Public method: A punch is pressed onto the partial surface of the system to be kept open, whereas the remaining surface of the system is sealed with viscous wrapping material.

Injection moulding method: Prefabricated injection moulded casings are used for selectively packing the systems.

For the electrical contacting or bonding of the system use is generally made of the wire bonding method, which is well known in microelectronics. In the known production processes for locally selectively packed systems use is consequently made of different processes for the electrical contacting and for the local, selective packing, which do not assist one another. This leads to long production times, higher equipment purchase prices, greater labour and personnel expenditure and ultimately higher product costs. The costs for the housing of such partly open systems can then represent a significant proportion of the total production costs.

A problem of the present invention is to provide a simple, reliable and cost-effective process for the application of a system to a substrate ensuring that at least one partial surface of the system is accessible for external influences and at least one other partial surface is protected against external influences. A further problem of the invention is to provide a device which can be produced in simple, inexpensive manner using said process.

The problem is solved by the process and device according to the invention, as defined in the independent claims.

A system, which is to be applied to a substrate, has at least one first partial surface, whose interaction with the environment is to be possible after performing the process, and at least one second partial surface, which is to be protected against external influences. In the process according to the invention, initially the substrate is prepared, at least one passage point suitable for the intended interaction being produced in the substrate. Such a passage point is preferably constructed as at least one opening in the substrate. The system and the substrate are so mutually positioned, that the at least one first partial surface faces the substrate and that the at least one passage point in the substrate and the at least one first partial surface come to rest facing one another. Contacts are produced at contact points provided, preferably with one of the known flip-chip technologies. The contacts link the system and the substrate mechanically and/or electrically, i.e. at least one contact can be electrically conductive. Outside the contacts the system and substrate normally have a spacing from one another such that at least one space or gap is formed.

The above-described basic form of the production process according to the invention already ensures local selective packing, i.e. the protection of the at least one second partial surface. The at least one second partial surface is e.g. protected against contact with external objects, liquid splashes from the outside, etc. However, for many applications a hermetic seal is required. According to the invention, a hermetic seal can be ensured using one of the three following variants.

In a first variant at least one contact is produced, which completely surrounds the at least one passage point in the substrate. Thus, such a sealing contact seals the at least one second partial surface in hermetic manner against external influences. The greatest advantage of this variant is that the same process is used for producing both the electrical contacting and for the local, selective packing, so that production is particularly simple, reliable and inexpensive.

In a second variant the gap between the system and the substrate is at least partly filled with an initially liquid or viscous filling material, whilst making use of capillary forces. In the vicinity of the at least one passage point in the substrate the capillary forces are too small or are completely missing, so that the filling material does not wet the at least one first partial surface. The filling material is subsequently cured and hermetically seals the at least one second partial surface against external influences, whereas the at least one first partial surface is open. The advantages of this variant are that the sealing is in certain circumstances more effective, because it is in full-surface form. The filling material simultaneously ensures an even better cohesion between system and substrate. In addition, the filling material compensates varying thermal expansions of the system and the substrate.

A third variant is constituted by the combination of the first and second variants. Thus, a sealing contact is produced around the at least one first partial surface and the at least one second partial surface is at least partly sealed with a sealing filling material. In this third variant the sealing contact need not necessarily completely surround the at least one passage point, but the at least one second partial surface is still hermetically sealed. An advantage of this variant is that the sealing contact serves as a barrier for the filling material, so as to define an exact boundary between the sealed and the unsealed area. The third variant also combines most of the advantages of the first two variants.

The device according to the invention producible by the aforementioned process can e.g. be used for flow sensors, viscosity sensors, moisture sensors, force sensors, pressure sensors, sensors for electromagnetic radiation, sensors for particle radiation or chemical sensors.

The invention is described in greater detail hereinafter relative to the attached drawings, wherein show:

FIGS. 1 to 5 Different steps in a first embodiment of the production process according to the invention, in cross-section.

Figure 6:
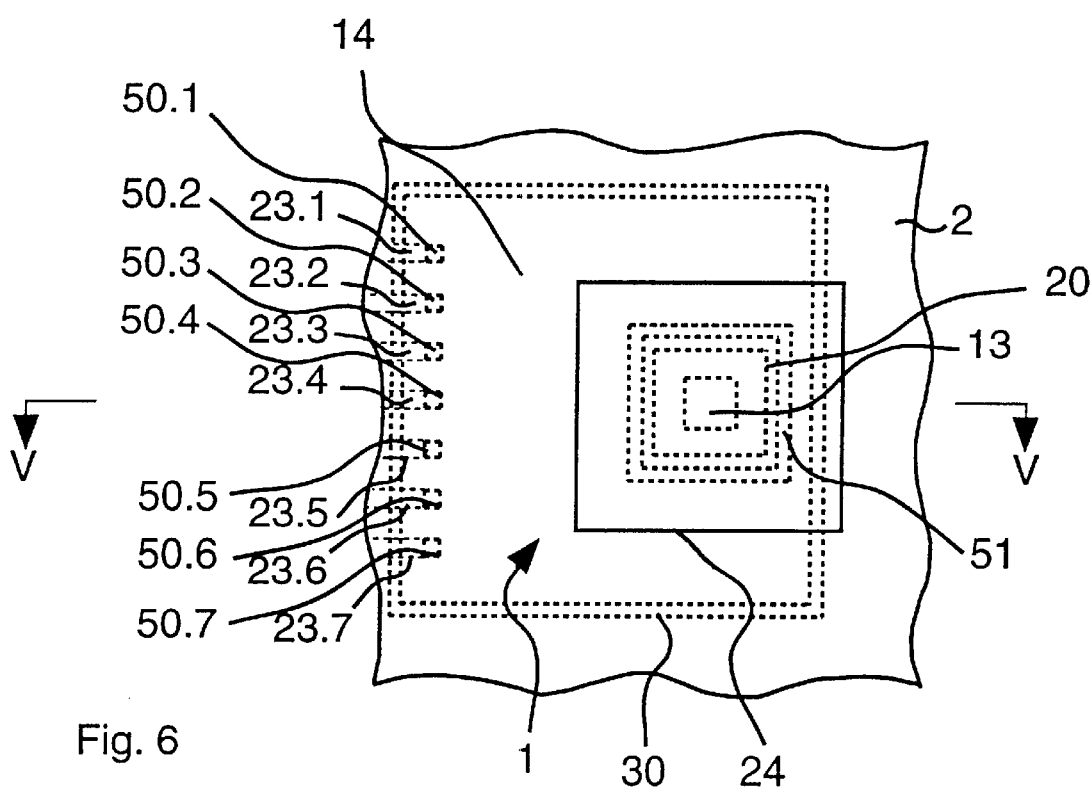

FIG. 6 A plan view of the first embodiment of the device according to the invention.

Figure 7:
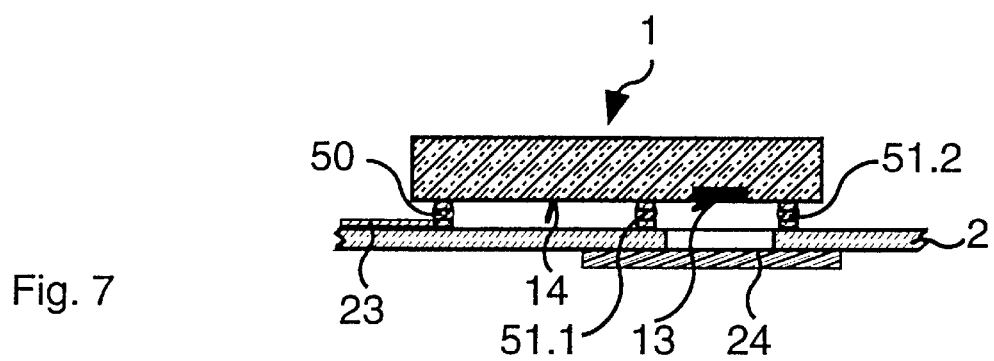

FIG. 7 A cross-section through a second embodiment of the device according to the invention.

Figure 8:
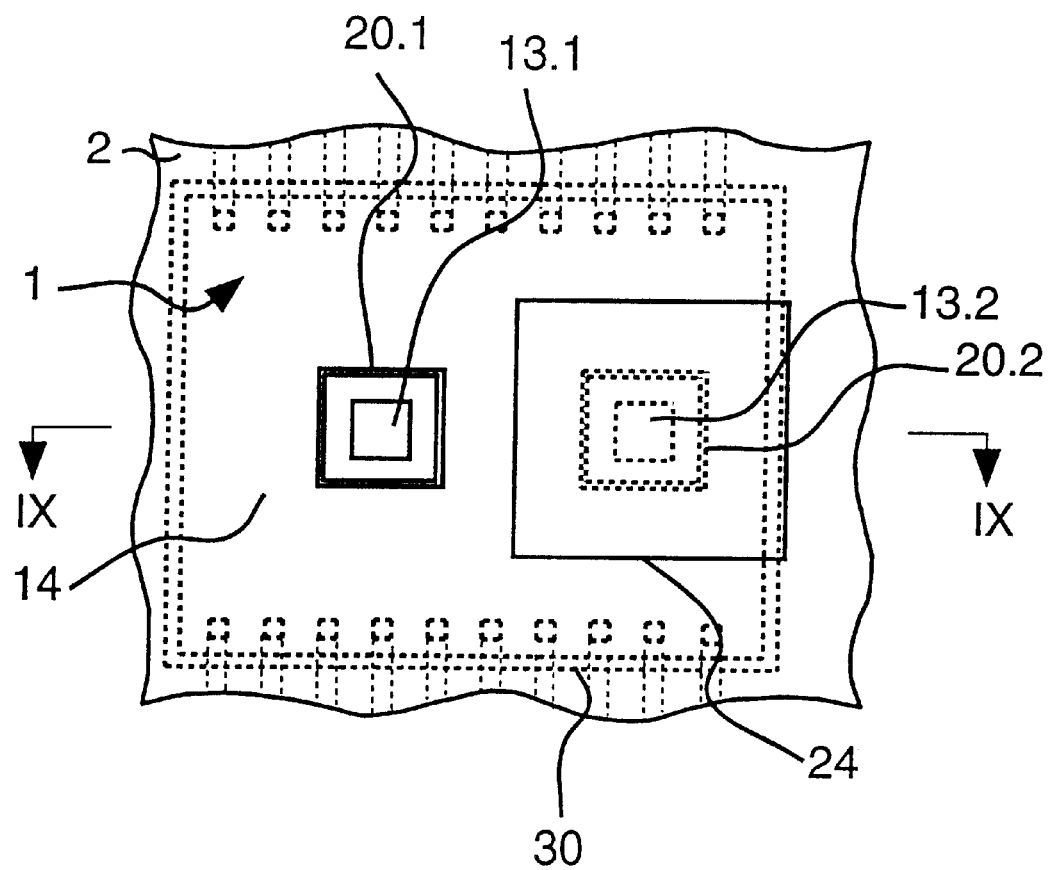
Figure 9:
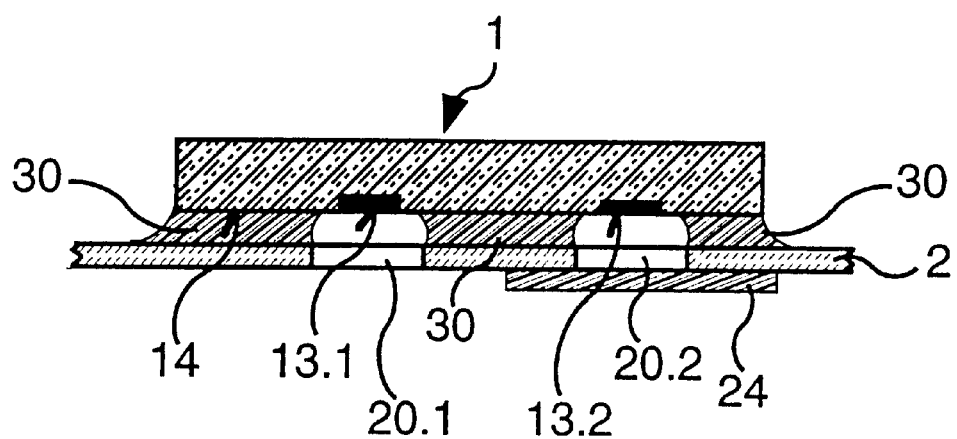

FIGS. 8 & 9 A plan view and a cross-section through a third embodiment of the device according to the invention.

Figure 10:
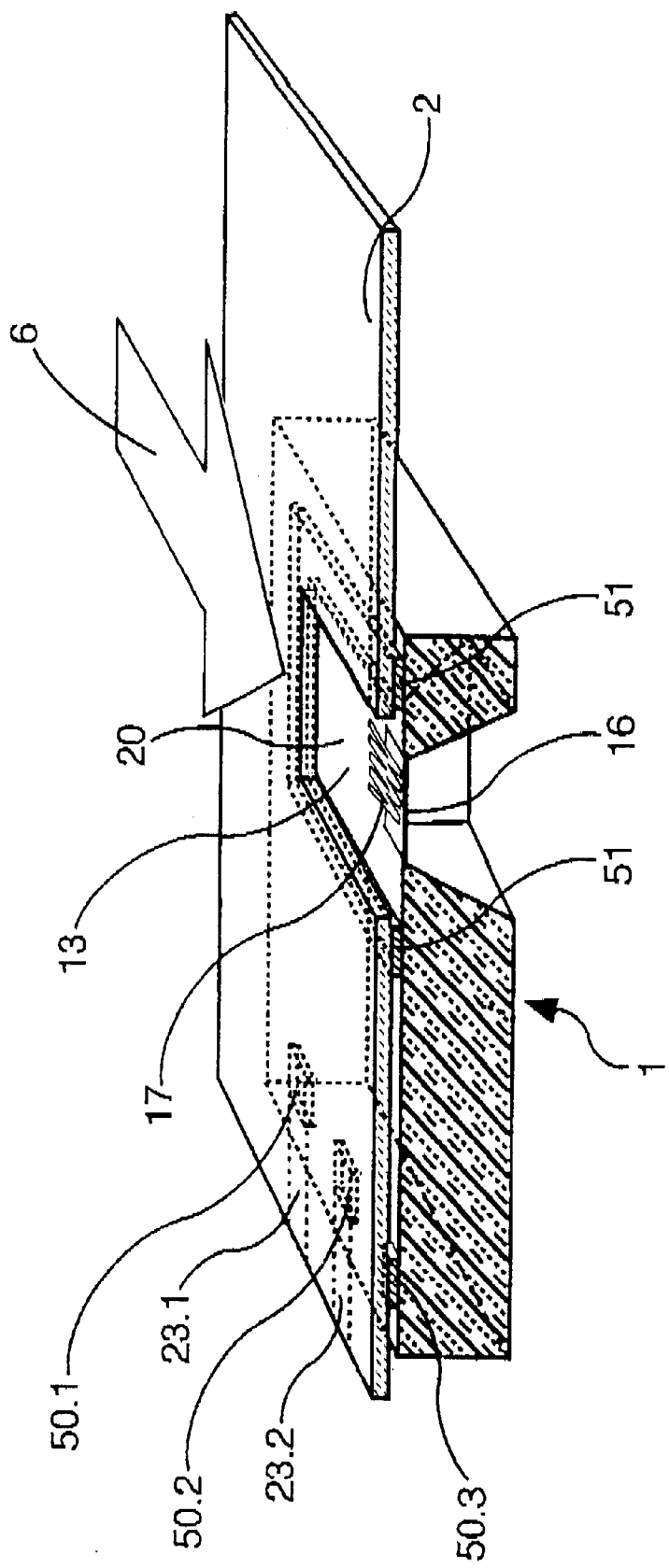

FIG. 10 A three-dimensional view of a flow sensor produced using the process according to the invention.

In order to facilitate understanding, in FIGS. 1 to 5, 7, 9 and 10 the heights with respect to the lengths are not shown to scale and in addition the heights of the individual elements are not necessarily in the correct mutual relationship.

FIGS. 1 to 5 diagrammatically show different steps of an embodiment of the production process according to the invention. The process steps can be performed in the order described here or in some other order. Cross-sections are shown through intermediates or through a finished product after the particular process step.

FIG. 1 diagrammatically shows a system 1 prepared for packing. It comprises a carrier 10, preferably made from a semiconductor material such as silicon. On at least one side 11 of the system are typically provided electronic, mechanical, thermal, chemical and/or other functional units, but they are not shown so as not to overburden the drawing. The functional units essentially determine the function of the system 1. They are produced by processes known from microelectronics and microsystem technology such as epitaxy, oxidation, photolithography, diffusion, ion implantation, metallization, anisotropic etching or other processes tailor-made to the particular use.

On one side 11 of the system 1 is provided a first partial surface 13, which is to be rendered accessible to external influences in the particular application. If the system 1 is e.g. a sensor, then the first partial surface 13 contains the sensitive surface of the sensor, on which acts externally a signal to be measured. Although in FIG. 1 only a single first partial surface 13 is shown, the system 1 can also have several first partial surfaces. A second partial surface 14 of the system is to be protected against external influences. In the case of a microsystem 1 with a sensor on the second partial surface 14 is e.g. provided evaluation electronics, which are neither to be influenced nor damaged by the signal to be measured or other external influences. On the same side 11 as the at least one first partial surface 13 and second partial surface 14 are provided prepared contact points 15.1–15.3, although the latter can be eliminated as a function of the contacting method.

Figure 2:
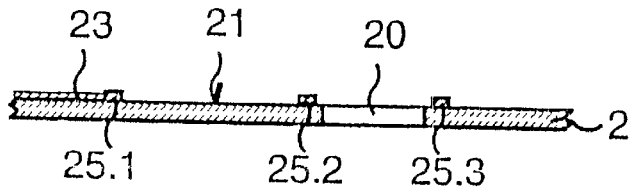

FIG. 2 diagrammatically shows a substrate 2 to which the system 1 is to be applied. The substrate 2 is e.g. made from ceramic, synthetic material such as e.g. epoxy resin, FR4, polyimide or some other synthetic material and is preferably constructed as a printed circuit board or PCB. It can e.g. be produced according to the DYCOstrate$^{(R)}$ method, as disclosed in WO92/15408 and WO93/26143. The substrate 2 is provided with at least one passage point 20, which corresponds to the at least one first partial surface 13 on the system 1. The at least one passage point 20 is such that it is suitable for the intended interaction with the environment of the at least one first partial surface 13. It can e.g. be constructed as one or more openings in the substrate 2, as a finely perforated substrate point, as a substrate point with other material characteristics, as a particularly thin substrate point, etc. For reasons of simplicity in the following drawings the passage point 20 is described or represented as an opening 20. Like the system 1, optionally the substrate 2 can have on one side 21 prepared contact points 25.1-25.3. The substrate 2 can be provided with electrical conductors 23, which c an e.g. be produced in PCB or thick film technology.

Figure 3:
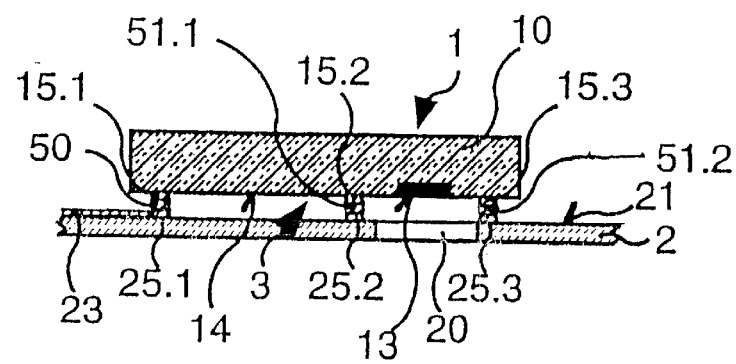

According to the inventive process shown in FIG. 3, the system I and substrate 2 are so mutually positioned that the first partial surface 13 faces the substrate 2, i.e. its side 21 possibly having contact points 25.1–25.3 and the opening 20 in substrate 2 and the first partial surface 13 face one another in such a way that the opening 20 leaves free the first partial surface 13. On the provided, optionally prepared contact points 15.1–15.3,25.1–25.3 are produced contacts 50, 51.1, 51.2, e.g. by soldering or by adhesion. The solder paste or adhesive can be applied e.g. by stencil printing, screen printing), dipping in molten solder or by electrodeposition on the contact points 15.1–15.3, 25.1–25.3. Such methods for the application and soldering of a semiconductor 1 to a substrate 2 are known as flip-clip technologies.

The contacts 5.1–5.3 50, 51,1, 51.2 call also serve to hold together the system 1 and substrate 2. However, it is advantageous to use the contacts 5.1–5.3 50, 51,1, 51.2 simultaneously for further functions. Certain contacts 50 can be provided for an electrical function and certain contacts 51.1, 51.2 for sealing the second partial surface 14. One contact can also fulfill several functions. If the contacts 51.1, 51.2 at opening 20 completely surround the latter, it forms a sealing contact at the embodiment of the inventive device shown in FIG. 3 corresponds to the first, aforementioned variant of a locally selective packing with hermetic sealing. Outside the contacts 50, 51.1, 51.2 the system 1 and substrate 2 normally have a spacing such that at least one space or gap 3 is formed.

Figure 4:
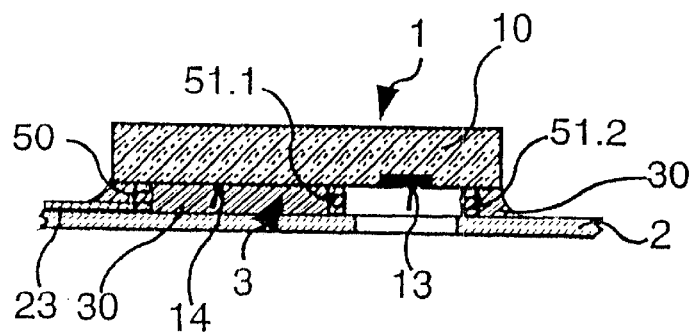

FIG. 4 shows an embodiment of the device according to the invention following a further, optional process step. In this process step the gap 3 between system I and substrate 2 is at least partly filled with an initially liquid or viscous filling material 30, whilst utilizing the capillary forces. In this embodiment the sealing contact 51.1, 51.2 prevents the filling material 30 from reaching the first partial surface 13. The filling material 30 is then cured and hermetically seals against external influences the second partial surface 14, whilst leaving open the first partial surface 13. An advantageous side effect of the filling material 30 is that it compensates the varying expansions of the system 1 and substrate 2. The carriers 10 of the system I and substrate 2 normally have different thermal expansions, which can have a disadvantageous effect on the long-term stability. The embodiment of the inventive device shown in FIG. 4 corresponds to the third, aforementioned variant of a locally selective packing with hermetic sealing.

Figure 5:
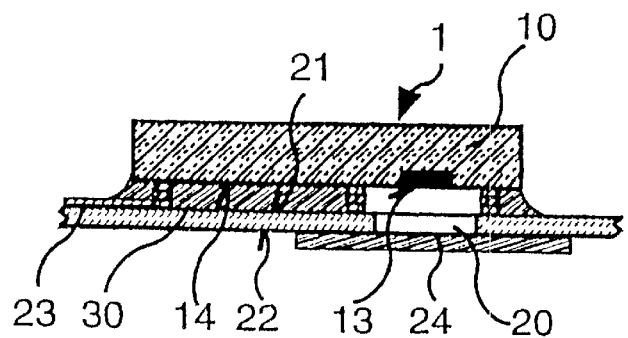

FIG. 5 shows an embodiment of the device according to the invention following a further, optional process step. In this step the opening 20 is covered with a selective cover 24. The cover 24 is selective in the sense that it permits the desired contact with the environment, e.g. permits the passage of the signal to be measured by the sensor to the sensitive sensor surface 13, but blocks undesired, external influences. In the case of infrared sensors the cover 24 could e.g. be an infrared transmission filter constructed in silicon wafer form and applied to the opening 20. In the case of moisture sensors the cover 24 could be a semipermeable membrane or semipermeable metal (e.g. porous aluminium). The cover 24 can be applied to the side 21 facing the system 1 or the side 22 remote from the system 1 via the opening 20 or also in said opening 20.

FIG. 6 is a plan view of a first embodiment of a device according to the invention. The line V—V indicates where the cross-sections shown in FIGS. 5 and 7 are made. A substrate 2 is provided with an opening 20, which ensures an interaction of the first partial surface 13 of a system 1 with the environment. In this embodiment the opening 20 is square, but can also have a different shape, e.g. rectangular or circular. In this embodiment a sealing contact 51 between the system 1 and substrate 2 surrounds the opening or first partial surface 13 in a complete manner and, together with the substrate 2, protects a second partial surface 14 against external influences. The sealing contact 51 forms a type of ring, which need not be circular, around the opening 20. Particularly when no hermetic seal is necessary, the contact 51 need not completely surround the opening 20. Electrical contacts 50.1–50.7 can be produced with the same process as the sealing contact 51. Conductors 23.1–23.7 are applied to the substrate 2.

The second partial surface 14 in FIG. 6 can be sealed with a filling material 30, which can be readily seen in FIGS. 4 and 5. However, if there is a sealing contact 51, there is no need for the filling material 30, because the sealing contact 51 already ensures, together with the substrate 2, that the second partial surface 14 is not accessible to external influences. Such a second embodiment of the inventive device without filling material is shown in cross-section in FIG. 7. The embodiment of the device according to the invention shown therein corresponds to the first, aforementioned variant of a locally selective packing with hermetic sealing.

FIG. 8 shows a third embodiment of the device according to the invention. This embodiment has no sealing contact and consequently corresponds to the second, aforementioned variant of a locally selective packing with hermetic sealing. The protection of the second partial surface 14 is ensured by filling material 30 between the system 1 and substrate 2, whereas the first partial surfaces 13.1, 13.2 are free under the openings 20.1, 20.2. The embodiment shown in FIG. 8 has two openings 20.1, 20.2, one opening 20.2 being provided with a selective cover 24, whereas the other opening 20.1 is not.

A cross-section along line IX—IX in FIG. 8 is shown in FIG. 9. Whilst utilizing the capillary forces, the gap between the system 1 and substrate 2 is filled with a liquid or viscous filling material 30, which is subsequently cured. In the vicinity of the openings 20.1, 20.2 the capillary forces are too small or completely missing, so that the first partial surfaces 13.1, 13.2 are not wetted with filling material 30.

Thus, even without a sealing contact, it is possible to ensure in simple manner that the first partial surfaces 13.1, 13.2 are accessible to external influences, whereas the second partial surface 14 is hermetically sealed, i.e. protected against external influences.

Finally, FIG. 10 shows a perspective, partly exposed view of a device according to the invention used as a gas flow sensor. The system 1 constructed as a sensor silicon chip is at the bottom and the ceramic substrate 2 at the top. A gas to be measured flows over the substrate, indicated by an arrow 6. The opening 20 in the substrate 2 allows the gas 6 to interact with a first partial surface 13 of the sensor chip 1. The first partial surface 13 contains a membrane 6 of dielectric layers. On the first partial surface 13 is located an integrated arrangement 17 of heating resistors and thermopiles and the signals of the latter constitute a measure for the gas flow 6.

In the production of the device of FIG. 10, contact points made from gold are prepared on the sensor chip 1 using a standard process known in connection with the manufacture of integrated circuits (IC's). The electrical conductors 23.1, 23.2 on the ceramic substrate 2 are produced by thick film technology. By stencil printing solder paste is applied to the prepared contact points and on joining together the sensor chip and ceramic substrate contacts 50.1–50.3, 51 are produced by soldering at the contact points. One contact 51 completely surrounds the opening 20 or the first partial surface 13 and serves as a sealing contact. Further contacts 50.1–50.3 are used for electrical contacting or bonding between the sensor chip 1 and ceramic substrate 2.

The process and device according to the invention can be used not only for gas flow sensors, but e.g. also for other flow, liquid, infrared, ultraviolet, light, chemical or pressure sensors.

What is claimed is:

1. A process for the application of a sensor or transducer to a substrate, comprising the following steps:

preparing the sensor or transducer, the sensor or transducer having at least one first partial surface comprising means for interacting with the environment and at least one second partial surface with electronic functional units;

preparing a substrate comprising at least one passage point;

mutually positioning the sensor or transducer and the substrate in such a way that said at least one first partial surface and said at least one second partial surface face the substrate and that said at least one passage point in the substrate and said at least one first partial surface face one another;

producing contacts which link the sensor or transducer and the substrate, between the sensor or transducer and the substrate.

2. The process according to claim 1 wherein the contacts between the sensor or transducer and the substrate are produced by flip-chip technology.

3. The process according to claim 1 wherein for the hermetic sealing of said at least one second partial surface of the sensor or transducer, which is to be protected against external influences, at least one contact is produced between the sensor or transducer and substrate and completely surrounds the at least one passage point in the substrate.

4. The process according to claim 1, wherein for the heretic sealing of the at least one second partial surface of the sensor or transducer, which is to be protected against external influences, a gap between the sensor or transducer and the substrate is at least partly filled with an initially liquid or viscous filling material.

5. The process according to claim 1, wherein for the hermetic sealing of said at least one second partial surface of the sensor or transducer, which second partial surface is to be protected against external influences, at least one contact is produced between the sensor or transducer and the substrate, which completely or partly surrounds the at lease one passage point in the substrate and a gap between the sensor or transducer and the substrate is at least partly filled with an initially liquid or viscous filling material.

6. The process according to claim 4, wherein capillary forces are used for filling the gap between the sensor or transducer and the substrate.

7. The process according to claim 4 wherein the filling material is cured during or alter sealing.

8. The process according to claim 1 wherein at least one opening is produced in the substrate as the passage point.

9. The process according to claim 8, wherein for keeping undesired, external influences away from the first partial surface, the at least one opening is covered with a selective cover.

10. A sensor or transducer device comprising:
  a sensor or transducer applied to a substrate, and at least one contact located between the sensor or transducer and the substrate;
  the substrate comprising a passage point;
  the sensor or transducer having at least one first partial surface comprising means for interacting with the environment;
  said passage point and said first partial surface facing one another;
  the sensor or transducer further having at least one second partial surface with electronic functional units;
  said second partial surface facing the substrate and being positioned opposite to at least part of the substrate.

11. The device according to claim 10 comprising one electrically conductive contact between the sensor or transducer and the substrate.

12. The device according to claim 10, comprising at least one sealing contact between the sensor or transducer and the substrate, which completely surrounds the at least one passage point in the substrate.

13. The device according to claim 10 comprising a gap between the sensor or transducer and the substrate, which gap is at least partly filled with a filling material.

14. The device according to claim 12 comprising at least one contact between the sensor or transducer and the substrate, which contact partly or wholly surrounds the at least one passage point in the substrate, a gap being formed between the sensor or transducer and the substrate, which gap is at least partly filled with a filling material.

15. The device according to claim 10 wherein the passage point is constructed as at least one opening in the substrate.

16. The device according to claim 15 comprising least one selective cover by means of which undesired, external influences can be kept away from the first, partial surface, the at lease one selective cover being located on, in or under the at least one opening.

17. The device according to claim 16, wherein the selective cover comprises porous metal or a semipermeable membrane.

18. The device according to claim 10 wherein the sensor or transducer is constructed as a semiconductor chip.

19. The device according to claim 10 wherein the substrate is made from ceramic, epoxy resin, FR4, polyimide or some other synthetic material.

20. The device according to claim 10 wherein the contacts are made from solder material or adhesive.

21. Use of the device according to claim 10 for flow sensors, viscosity sensors, moisture sensors, force sensors, pressure sensors, sensors for electromagnetic radiation, sensors for particle radiation or chemical sensors.

* * * * *